United States Patent [19]
Cloughley et al.

[11] Patent Number: 5,696,163
[45] Date of Patent: Dec. 9, 1997

[54] METHOD OF STABILIZING POLYUNSATURATES

[75] Inventors: John B. Cloughley, Halwhistle; Bertram J. F. Hudson, Reading, both of England; Ian Law, Chaolais, Scotland

[73] Assignee: Scotia Holdings plc, Surrey, England

[21] Appl. No.: 527,013

[22] Filed: Sep. 12, 1995

Related U.S. Application Data

[63] Continuation of Ser. No. 77,994, Jun. 18, 1993, abandoned.

[30] Foreign Application Priority Data

Jun. 23, 1992 [GB] United Kingdom ............... 9213322

[51] Int. Cl.$^6$ ............ A61K 31/225; A61K 31/355; A61K 31/20
[52] U.S. Cl. .............. 514/547; 514/458; 514/559; 514/560
[58] Field of Search ............... 514/547, 559, 514/560, 458; 426/330.6, 541, 654

[56] References Cited

U.S. PATENT DOCUMENTS

| | | | |
|---|---|---|---|
| 5,015,483 | 5/1991 | Haynes et al. | 426/73 |
| 5,077,069 | 12/1991 | Chang et al. | 426/330.6 |

FOREIGN PATENT DOCUMENTS

| | | |
|---|---|---|
| 15-073/92 | 11/1992 | Australia . |
| 0287281 | 10/1988 | European Pat. Off. . |
| 0326829 | 8/1989 | European Pat. Off. . |
| 2123024 | 1/1984 | United Kingdom . |
| 92/10207 | 5/1993 | WIPO . |

OTHER PUBLICATIONS

*Database WPIL*, Week 8714, Derwent Publications Ltd., London, GB; AN 87-097612 & JP-A-62 045 336 (Toyo Beauty KK) Feb. 27, 1987.

Chemical Abstracts (97:31713p) 1982 Bourgeois et al.

*Primary Examiner*—Kevin E. Weddington
*Attorney, Agent, or Firm*—Nixon & Vanderhye P.C.

[57] ABSTRACT

Method of stabilizing polyunsaturates by adding thereto (i) ascorbic acid or an ester or salt thereof, and (ii) a phosphorylated mono- or di-fatty acyl glyceride or a salt thereof, and optionally a tocopherol or tocotrienol antioxidant, and a method of preparing stable pharmaceutical, nutritional or veterinary compositions.

5 Claims, No Drawings

METHOD OF STABILIZING POLYUNSATURATES

This is a continuation of application Ser. No. 08/077,994, filed Jun. 18, 1993, now abandoned.

This invention is concerned with antioxidants.

Polyunsaturated materials are readily susceptible to spoilage by mild oxidation such as by contact with atmospheric oxygen and antioxidants are required.

Most oils of natural occurrence, especially vegetable oils, already contain antioxidants, most commonly phenolic compounds such as tocopherols. In some cases however especially when the levels of natural antioxidants have been reduced by refining or other processing it is advantageous to supplement residual antioxidants by the addition of like compounds, of natural or synthetic origin.

Furthermore other chemically dissimilar substances, which in their own right may or may not also have antioxidant properties, in many cases enhance the overall antioxidant effect more markedly than would be expected from an additive consideration of the separate effects. Many substances have been claimed to act as such synergists under specified conditions. For example ascorbic acid and its esters and salts are well known synergists for primary antioxidants such as the tocopherols.

Phosphatidic acids and their salts and esters have already been shown to behave as synergists under certain conditions with antioxidants that may either be present naturally in polyunsaturated oils or may be added to such oils (GB 2 123 024 A, published 25 Jan. 1984). The disclosure in this specification is however primarily concerned with stability related to high temperature use, as in cooking oils. Further it does not concern the triply and more highly ethylenically unsaturated materials that are particularly valuable components in many natural oils. Such polyunsaturates, as they are referred to herein, are highly susceptible to oxidation even at room temperature.

It has now been found, in accordance with the present invention, that a remarkable antioxidant effect (on polyunsaturates) is given by phosphatidic acids or salts thereof in combination with ascorbic acid or its salts or esters preferably with long chain fatty acids. Ascorbyl palmitate or ascorbyl stearate for example, in combination with the phosphatidic acids, can delay ambient-temperature oxidation of polyunsaturated fatty acids or their esters such as glyceride oils to give a very extended spoilage time under ordinary commercial conditions. Furthermore the presence of endogenous tocopherols and/or tocotrienols or the addition of small mounts of purified alpha-tocopherol can further enhance the protective effect.

The phosphatidic acids are phosphorylation products of long-chain motto- or di-glycerides or mixtures thereof, prepared by the interaction of a phosphorylating agent such as phosphorus pentoxide with for example vegetable seed oils such as sunflower, rape, safflower etc. They can comprise a complex mixture of chemical species produced by splitting of fatty acyl residues from the triglycerides in the starting material, and replacement by phosphate groups. The preferred chain length is $C_{12}$ or more, preferably $C_{16}$, up to $C_{22}$ or higher, according to the fatty acyl residues present in the initial triglyceride.

Ascorbic acid and its esters may be of natural or synthetic origin but long chain esters such as those discussed in the preceding paragraph are preferred because they are more soluble in oils than ascorbic acid itself or its short chain esters.

The present invention is distinguished from previous proposals concerned with glyceride oil stabilisation in that it is primarily concerned with long term stabilisation at ambient temperatures, and with polyunsaturated fatty acids and their esters rather than much more easily stabilised materials of lower degrees of unsaturation.

The stability of edible oils is usually judged by means of an accelerated test conducted at 100° C. or above that seeks to effect rapid oxidation. For oils designed for frying, baking or other culinary purposes this is realistic. However if oils are specifically for storage and consumption at ambient temperatures such as for salad dressings or for medicinal or pharmaceutical applications such tests are not realistic. Not only does the oxidation mechanism change in character as the temperature is raised but polyunsaturated acids themselves undergo chemical changes at elevated temperatures that may have adverse effects on their biological properties. Accordingly an accelerated room temperature test has been developed which is appropriate to the evaluation of edible oils particularly susceptible to oxidation by atmospheric oxygen.

In this test, which is called the open dish test, oil is exposed in a thin layer in a Petri dish of about 10 cm diameter to atmospheric oxygen at room or other temperature. The rate of spoilage is measured by determining peroxide values periodically usually over a period of several days. The time needed for the peroxide value to treble its original value is a useful quantitative measure to compare rates of spoilage and is known as $T_3$.

The rate of oxidation of an edible oil is primarily determined by the number and position of the double bonds in the molecule. In general molecules with one or two double bonds such as oleic and linoleic acid deteriorate progressively on long term storage. If three double bonds are present however, as for example in gamma linolenic acid, deterioration is much more rapid and stabilisation becomes essential. If there are more than three double bonds as in some animal fats and in marine oils spoilage is very rapid indeed and stabilisation is difficult to achieve.

The following Examples illustrate the invention.

EXAMPLE 1

Freshly extracted unrefined evening primrose oil with a peroxide value (PV) of 10.2 oxidised progressively in the open dish test with a $T_3$ of 23 days. The addition of 0.5% of phosphorylated mono-/di- glycerides of partially hardened rapeseed oil (hereafter PMDG) extended the $T_3$ to 33 days. Likewise the alternative addition of 0.1% of ascorbyl palmitate (AP) extended the $T_3$ to 45 days. However when both of these stabilisers were added simultaneously the $T_3$ was extended to about 300 days. If the extension of the $T_3$ had taken place on an additive basis a $T_3$ of about 55 days at most would have been expected for the combination.

EXAMPLE 2

Refined decolourised evening primrose oil with an initial PV of 1.8, which contained only 0.015 to 0.02% of residual total tocopherols, had a PV of 6.0 and a $T_3$ of 2 days in the open dish test. The addition of 0.1% AP and 0.5% PMDG reduced the PV to 1.3 after 2 days and to 3.9 after 12 days exposure. The further simultaneous addition of 0.005% of a highly purified preparation of α-tocopherol suppressed the increase of PV even more effectively, to 1.1 after 2 days and 1.5 after 12 days exposure.

EXAMPLE 3

A freshly rendered fish oil with an original PV of 8.6 oxidised very rapidly in the open dish test, giving a $T_3$ value of 6 days. The addition of 0.1% of AP extended the $T_3$ to 10 days and that of 0.5% of PMDG to 11 days. However the addition of both of these substances simultaneously extended the $T_3$ to 60 days, demonstrating substantial synergism. If there had been no synergism, a $T_3$ of about 15 days might have been expected.

EXAMPLE 4

A concentrate of gamma-linolenic acid, 'GLA 70', containing 70% of this acid and no traces of native tocopherols, and therefore much more susceptible to oxidation than natural products with smaller concentrations had an original PV of 3.4. In the open dish test it afforded a $T_3$ of 10 days which could be extended to 25 days by the addition of 0.1% of AP and to 17 days by the addition of 0.5% of PMDG. However when both of these additives were present simultaneously the $T_3$ increased to 85 in contrast to the expected $T_3$ of about 32 if the separate stabilisation effects of the two components had been merely additive.

EXAMPLE 5

A refined evening primrose oil with an original PV of 5.9, after submission to the open-dish exposure test at 37° C. deteriorated to such an extent that its PV was 47.6 after 5 days and 87.0 after 12 days. However, the same oil after supplementation with 0.1% AP and 0.5% of the sodium salt of PMDG was stabilised to such an extent that under the same conditions the PV was only 4.3 after 5 days exposure and 8.6 after 12 days exposure.

EXAMPLE 6

A concentrate of eicosapentaenoic acid, 'EPA 50' containing 50% of this quintuply unsaturated essential fatty acid in the free acid form and no natural antioxidant, immediately after manufacture, had a PV of 1.2. In the open-dish test the extreme susceptibility of this polyunsaturated concentrate to oxidation was demonstrated in that after two days the PV was over 200. However when 0.1% of ascorbyl stearate and 0.5% of the sodium salt of PMDG were present together in the oil it was stabilised to such an extent that the PV after 2 days was only 1.6 and after 7 days was still less than 2.

EXAMPLE 7

Ethyl esters derived from an oil extracted from fungal biomass rich in arachidonic acid and having no detectable tocopherol content increased rapidly in PV in the open dish test from an initial 4.4 to 85.5 after 4 days. The same oil after the addition of 0.05% of ascorbic acid and 0.2% of the sodium salt of PMDG, had a PV of only 7.8 under the same conditions.

We claim:

1. A method of stabilizing polyunsaturates comprising fatty acids of the n-6 series with 3 or more double bonds or fatty acids of the n-3 series with 4 or more double bonds susceptible to ambient temperature atmospheric oxidation, which method comprises adding to the polyunsaturate (i) 0.02 to 0.2% by weight of the composition of ascorbic add as such or in the form of an ester or salt, (ii) 0.1 to 1.0% by weight of the composition of a phosphorylated mono- or di-fatty acyl glyceride (PMDG) as such or in the form of a salt, and optionally (iii) 0.001 to 0.1% by weight of the composition of a tocopherol or tocotrienol antioxidant.

2. The method as claimed in claim 1 wherein the mount of tocopherol or tocotrienol antioxidant is 0.01 to 0.02% by weight of the composition.

3. The method as claimed in claim 1, in which PMDG is present in the composition in the form of the ammonium or sodium salt.

4. The method as claimed in claim 1, in which the composition contains ascorbic acid in the form of ascorbyl palmitate or stearate.

5. The method as claimed in claim 1 wherein the mount of ascorbic acid or ester in 0.05 to 0.1% by weight of the composition.

\* \* \* \* \*